(12) United States Patent
Everaert et al.

(10) Patent No.: US 7,947,259 B2
(45) Date of Patent: May 24, 2011

(54) HAIR CARE COMPOSITIONS

(75) Inventors: Emmanuel Paul Jos Marie Everaert, Wirral (GB); Jordan Todorov Petkov, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 542 days.

(21) Appl. No.: 11/658,757

(22) PCT Filed: Jul. 1, 2005

(86) PCT No.: PCT/EP2005/007237
§ 371 (c)(1),
(2), (4) Date: Jan. 26, 2007

(87) PCT Pub. No.: WO2006/010440
PCT Pub. Date: Feb. 2, 2006

(65) Prior Publication Data
US 2008/0317695 A1 Dec. 25, 2008

(30) Foreign Application Priority Data

Jul. 27, 2004 (EP) .................................... 04254484

(51) Int. Cl.
*A61Q 5/02* (2006.01)
(52) U.S. Cl. ................ 424/70.19; 424/70.21; 424/70.24
(58) Field of Classification Search ........................ None
See application file for complete search history.

(56) References Cited

U.S. PATENT DOCUMENTS

| | | | | |
|---|---|---|---|---|
| 5,510,384 A | * | 4/1996 | McKee et al. ................. | 514/530 |
| 5,556,616 A | * | 9/1996 | Janchitraponvej et al. ........................ | 424/70.122 |
| 6,153,569 A | | 11/2000 | Halloran ........................ | 510/119 |
| 7,041,627 B2 | * | 5/2006 | Kruse et al. ................... | 510/123 |

FOREIGN PATENT DOCUMENTS

| | | |
|---|---|---|
| EP | 0 191 564 | 10/1991 |
| EP | 0 473 349 | 3/1992 |
| EP | 0473349 * | 3/1992 |
| EP | 0 473 349 B1 | 5/1995 |
| JP | 95 015116 | 1/1995 |
| JP | 94 055656 | 3/2007 |
| WO | 95/20939 | 8/1995 |
| WO | 97/05232 | 2/1997 |
| WO | 98/04241 | 2/1998 |
| WO | 98/31327 | 7/1998 |
| WO | 99/44568 | 9/1999 |

OTHER PUBLICATIONS

Kawaguchi and Kubota, 2004. Rheo-optical properties of silicone oil emulsions in the presence of polymer emulsifiers. Langmuir, vol. 20:1126-1129.*
Dow, 2002. Water Soluble Resins, Dow Chemical, pp. 1-24; as disclosed by applicant in the Jun. 13, 2007 IDS.*
Laba, 1993. Rheological properties of Cosmetics and Toiletries, Cosmetic Science and Technology Series, vol. 13:81-98.*
Derwent Abstract of JP 04 348199, published Dec. 3, 1992.
"*Polvox Water-Soluble Resins*", Amerchol Dox Chamical Society, May 2002.
"Synergistic effects of high molecular weight polyethylene oxide (PEO) and cationic cellulosic polymers on conditioning properties of hair and skin care products", Wing Li et al., Cosmetics and Toiletries Manufacture Worldwide, Mar. 17, 2004, pp. 31-35.
Encyclopedia of Shampoo Ingredients, Anthony L.L. Hunting, 1983. *Cellulose Gum*, pp. 175.
Methocel® Cellulose Ethers and their Applicattons in Personal Care Products, 1989, 8 pages.
Hair and Hair Care, Marcel Dekker, Inc., p. 57, 1997.
European Opposition Statement (in German).

* cited by examiner

*Primary Examiner* — Jyothsna A Venkat
(74) *Attorney, Agent, or Firm* — Ronald A. Koatz

(57) ABSTRACT

The invention provides a hair care composition comprising a water-soluble, nonionic polymer of ethylene oxide and a water-soluble, nonionic cellulose ether.

2 Claims, No Drawings

HAIR CARE COMPOSITIONS

FIELD OF THE INVENTION

This invention relates to hair care compositions, in particular rinse-off hair care compositions such as shampoos and conditioners, which incorporate water-soluble nonionic polymers.

BACKGROUND AND PRIOR ART

Rinse-off hair care compositions typically comprise one or more surfactants for cleansing purposes and one or more conditioning agents, so as to provide a combination of cleansing and conditioning to the hair. Typically, these conditioning agents are water-insoluble oily materials, cationic polymers or cationic surfactants.

A problem associated with such rinse-off hair care compositions is that for many consumers they do not provide a sufficient level of "wet" sensory benefits, such as improved hair feel during washing.

The present inventors have found that a combination of certain water-soluble nonionic polymers improves wet sensory benefits significantly when they are incorporated into rinse-off hair care compositions such as shampoos. Compositions of the invention also show a surprising improvement in ease of rinsing.

Water-soluble nonionic polymers have been described for example in WO99/44568, which relates to the use of water-soluble nonionic polyethyleneoxide homopolymers to increase hair body and fullness when formulated in a high pH medium and applied to fine hair. The described polymers have molecular weights ranging from 100,000 (PEG-2M) to 5,000,000 (PEG-115M), preferably 300,000 (PEG-7M). They are said to deposit under the hair cuticle and provide it with more surface roughness and texture.

WO95/20939 describes thickened cream rinse emulsions formed from a combination of fatty alcohol with polyethyleneoxide homopolymers of molecular weight ranging from 100,000 (PEG-2M) up to 600,000 (PEG-14M). The compositions are said inter alia to enhance glossiness of the hair and provide dry combing benefits.

JP 95015116 describes a detergent composition having high washing and foaming power containing surfactant and 0.1 to 2 wt % hydroxypropylmethylcellulose.

JP 94055656 describes a hair cosmetic, such as a conditioner or rinse, containing quaternary ammonium salt, oil and nonionic cellulose ether derivative. The composition has a smoothing and softening effect on hair.

EP 0 191 564 describes a shampoo composition comprising a fatty acid ester of sucrose and a nonionic cellulose ether derivative such as hydroxyethylcellulose, hydroxypropylcellulose, hydroxypropylmethylcellulose and methylcellulose. The composition provides creamy foam and improves hair "flyaway".

U.S. Pat. No. 6,153,569 describes optically clear shampoo compositions containing aminofunctional silicone microemulsions and a thickener which can be a cellulose derivative such as methylcellulose, methylhydroxypropylcellulose, or hydroxypropylcellulose.

WO98/31327 describes nonionic water-soluble polymers such as cellulose ethers in the form of a separate phase of aqueous polymer droplets suspended in an aqueous surfactant phase, for improved hair and skin conditioning and clean feel.

SUMMARY OF THE INVENTION

The present invention provides a hair care composition comprising a water-soluble, nonionic polymer of ethylene oxide and a water-soluble, nonionic cellulose ether.

DETAILED DESCRIPTION

Water-Soluable, Nonionic Polymer of Ethylene Oxide

The hair care composition of the invention comprises a water-soluble, nonionic polymer of ethylene oxide.

As used herein, "water-soluble" refers to any material that is sufficiently soluble in water to form a clear or translucent solution to the naked eye at a concentration of 1.0% or more by weight of the material in water at 25° C.

Suitable polymers of ethylene oxide for use in the hair care compositions of the invention are linear homopolymers of ethylene oxide characterised by the general formula:

$$H(OCH_2CH_2)_nOH$$

These materials are generally termed polyethyleneoxides (or alternatively, polyoxyethylenes, or polyethylene glycols).

In the above general formula, n has an average value of at least 2000, preferably from 2,000 to 235,000 more preferably from 45,000 to 185,000, most preferably from 130,000 to 185,000.

Suitably, the weight average molecular weight ($M_w$) of the polymer of ethylene oxide ranges from 100,000 to 10 million daltons, preferably from 1 million to 10 million daltons, more preferably from 6 million to 10 million daltons, most preferably from 7 million to 8 million daltons.

As used herein, the weight average molecular weight ($M_w$) of a polymer is the summation of the number of polymer molecules and the squared sum of the individual polymer molecules' molecular weight, divided by the summation of the number of polymer molecules and the sum of the individual polymer molecules' molecular weight.

The $M_w$ of polyethyleneoxides corresponding to the above general formula can be determined by measuring their intrinsic viscosity in water at 30° C. The intrinsic viscosity, [η], is correlated to the $M_w$ of the polyethyleneoxide, and can be expressed by the following equation: $[\eta]=1.25\times10^{-4} M_w^{0.78}$.

Examples of commercially available polyethyleneoxides suitable for use in the hair care compositions of the invention include, but are not limited to, those polyethyleneoxides which are sold under the tradenames POLYOX® and UCARFLOC®, and which are available from the Amerchol Corporation or its associated companies.

Specific examples of such polyethyleneoxides include POLYOX® WSR-N10 which has a $M_w$ of 100,000 daltons; POLYOX® WSR-N80 which has a $M_w$ of 200,000 daltons; POLYOX® WSR-N750 which has a $M_w$ of 300,000 daltons; POLYOXS WSR-N3000 which has a $M_w$ of 400,000 daltons; POLYOX® WSR-205 which has a $M_w$ of 600,000 daltons; POLYOX® WSR-N12K which has a $M_w$ of 1 million daltons; POLYOX® WSR-301 which has a $M_w$ of 4 million daltons; POLYOX® WSR-303 which has a $M_w$ of 7 million daltons; POLYOX® WSR-308 which has a $M_w$ of 8 million daltons; UCARFLOC® Polymer 304 which has a $M_w$ of 7 million daltons; UCARFLOC® Polymer 309 which has a $M_w$ of 8 million daltons; UCARFLOC® Polymer 310 which has a $M_w$ of 10 million daltons; and mixtures thereof.

Of the above polyethyleneoxides, preferred are those materials with an $M_w$ of at least 6 million daltons, more preferably from 6 million to 10 million daltons, most preferably from 7 million to 8 million daltons.

The total amount of water-soluble, nonionic polymer of ethylene oxide (as described above) in hair care compositions of the invention generally ranges from 0.001 to 1%, preferably from 0.01 to 0.25%, more preferably from 0.02 to 0.2% by total weight polymer of ethylene oxide based on the total weight of the composition. Higher levels than this are preferably avoided since this can impart an undesirably stringy or slimy feel to the composition.

Water-Soluable, Nonionic Cellulose Ether

The hair care composition of the invention comprises a water-soluble, nonionic cellulose ether.

By "water-soluble" is meant any material that is sufficiently soluble in water to form a clear solution to the naked eye at a concentration of 1.0% or more by weight of the material in water at 25° C., as described above.

Preferred water-soluble nonionic cellulose ethers are methylcellulose and hydroxypropyl methylcellulose. These materials are manufactured by heating cellulose fibres with caustic solution which in turn is treated with methyl chloride, yielding the methyl ether of cellulose. Methylcellulose is made using only methyl chloride. For hydroxypropyl methylcellulose, propylene oxide is used in addition to methyl chloride to obtain hydroxypropyl substitution on the anhydroglucose units. This substituent group, —$OCH_2CH(OH)$—$CH_3$, contains a secondary hydroxyl on the number two carbon. The amount of substituent groups on the anhydroglucose units influences the solubility properties of the cellulose ether. Accordingly, suitable methylcelluloses and hydroxypropyl methylcelluloses for use in the hair care composition of the invention have a sufficient degree of methoxyl or methoxyl/hydroxypropyl substitution to cause them to be water-soluble as defined above.

Methyl cellulose and hydroxypropyl methylcellulose are commercially available in a number of viscosity grades from Dow Chemical as their METHOCEL trademark series. Hydroxypropyl methylcellulose is most preferred, and is available from Dow Chemical as their METHOCEL E, F, J, K and 40-Series products.

Generally the viscosity of the water-soluble, nonionic cellulose ether ranges from 100 to 100,000, preferably from 4,000 to 75,000 mPa·s for a 2% aqueous solution at 20° C., measured by Ubbelohde tube viscometer.

Examples of preferred commercially available materials are METHOCEL 40-100, METHOCEL 40-101 and METHOCEL 40-202 from Dow Chemical.

Mixtures of any of the above water-soluble nonionic cellulose ethers may also be suitable.

Water-soluble nonionic cellulose ether will generally be present in compositions of the invention at levels of from 0.01 to 2.0%, preferably from 0.1 to 0.5%, more preferably from 0.1 to 0.3%, by total weight of cellulose ether based on the total weight of the composition.

Product Form

Compositions of the invention are typically "rinse-off" compositions to be applied to the hair and then rinsed away.

A particularly preferred product form is a shampoo composition.

Shampoo Composition

Shampoo compositions of the invention are generally aqueous, i.e. they have water or an aqueous solution or a lyotropic liquid crystalline phase as their major component.

Suitably, the composition will comprise from 50 to 98%, preferably from 60 to 90% water by, weight based on the total weight of the composition.

Anionic Cleansing Surfactant

Shampoo compositions' according to the invention will generally comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphates, alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in shampoo compositions of the invention include sodium oleyl succinate, ammonium lauryl sulphosuccinate, sodium lauryl sulphate, sodium lauryl ether sulphate, sodium lauryl ether sulphosuccinate, ammonium lauryl sulphate, ammonium lauryl ether sulphate, sodium dodecylbenzene sulphonate, triethanolamine dodecylbenzene sulphonate, sodium cocoyl isethionate, sodium lauryl isethionate, lauryl ether carboxylic acid and sodium N-lauryl sarcosinate.

Preferred anionic cleansing surfactants are sodium lauryl sulphate, sodium lauryl ether sulphate(n)EO, (where n is from 1 to 3), sodium lauryl ether sulphosuccinate(n)EO, (where n is from 1 to 3), ammonium lauryl sulphate, ammonium lauryl ether sulphate(n)EO, (where n is from 1 to 3), sodium cocoyl isethionate and lauryl ether carboxylic acid (n) EO (where n is from 10 to 20).

Mixtures of any of the foregoing anionic cleansing surfactants may also be suitable.

The total amount of anionic cleansing surfactant in shampoo compositions of the invention generally ranges from 0.5 to 45%, preferably from 1.5 to 35%, more preferably from 5 to 20% by total weight anionic cleansing surfactant based on the total weight of the composition.

Further Ingredients

Optionally, a shampoo composition of the invention may contain further ingredients as described below to enhance performance and/or consumer acceptability.

Co-surfactant

The composition can include co-surfactants, to help impart aesthetic, physical or cleansing properties to the composition.

An example of a co-surfactant is a nonionic surfactant, which can be included in an amount ranging from 0.5 to 8%, preferably from 2 to 5% by weight based on the total weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies from about 1.1 to about 2. Most preferably the value of n lies from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl)glucamide.

A preferred example of a co-surfactant is an amphoteric or zwitterionic surfactant, which can be included in an amount ranging from 0.5 to about 8%, preferably from 1 to 4% by weight based on the total weight of the composition.

Examples of amphoteric or zwitterionic surfactants include alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine, lauryl betaine, cocamidopropyl betaine and sodium cocoamphoacetate.

A particularly preferred amphoteric or zwitterionic surfactant is cocamidopropyl betaine.

Mixtures of any of the foregoing amphoteric or zwitterionic surfactants may also be suitable. Preferred mixtures are those of cocamidopropyl betaine with further amphoteric or zwitterionic surfactants as described above. A preferred further amphoteric or zwitterionic surfactant is sodium cocoamphoacetate.

The total amount of surfactant (including any co-surfactant, and/or any emulsifier) in a shampoo composition of the invention is generally from 1 to 50%, preferably from 2 to 40%, more preferably from 10 to 25% by total weight surfactant based on the total weight of the composition.

Cationic Polymers

Cationic polymers are preferred ingredients in a shampoo composition of the invention for enhancing conditioning performance.

Suitable cationic polymers may be homopolymers which are cationically substituted or may be formed from two or more types of monomers. The weight average ($M_w$) molecular weight of the polymers will generally be between 100 000 and 2 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl(meth)acrylate, vinyl caprolactone and vinyl pyrrolidine. The alkyl and dialkyl substituted monomers preferably have $C_1$-$C_7$ alkyl groups, more preferably $C_{1-3}$ alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo- and co-polymers of unsaturated carboxylic acids having from 3 to 5 carbon atoms, (as described in U.S. Pat. No. 4,009,256);
cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions of the invention include monomers of the formula:

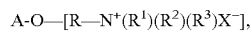

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR C14, JAGUAR C15, JAGUAR C17 and JAGUAR C16 Jaguar CHT and JAGUAR C162.

Mixtures of any of the above cationic polymers may be used.

Cationic polymer will generally be present in a shampoo composition of the invention at levels of from 0.01 to 5%, preferably from 0.05 to 1%, more preferably from 0.08 to 0.5% by total weight of cationic polymer based on the total weight of the composition.

Suspending Agent

Preferably an aqueous shampoo composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent will generally be present in a shampoo composition of the invention at levels of from 0.1 to 10%, preferably from 0.5 to 6%, more preferably from 0.9 to 4% by total weight of suspending agent based on the total weight of the composition.

Conditioner Compositions

Another preferred product form for compositions in accordance with the invention is a conditioner for the treatment of hair (typically after shampooing) and subsequent rinsing.

Such conditioner compositions will typically comprise one or more conditioning surfactants which are cosmetically acceptable and suitable for topical application to the hair.

Suitable conditioning surfactants include those selected from cationic surfactants, used singly or in admixture.

Preferably, the cationic surfactants have the formula $N^+R^1R^2R^3, R^4$ wherein $R^1$, $R^2$, $R^3$ and $R^4$ are independently ($C_1$ to $C_{30}$) alkyl or benzyl. Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl. More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (e.g.; Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Another example of a class of suitable cationic surfactants for use in the invention, either alone or together with one or more other cationic surfactants, is a combination of (i) and (ii) below:

(i) an amidoamine corresponding to the general formula (I):

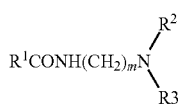

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and (ii) an acid.

As used herein, the term hydrocarbyl chain means an alkyl or alkenyl chain.

Preferred amidoamine compounds are those corresponding to formula (I) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylmine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof.

Particularly preferred amidoamines useful herein are stearamidopropyldimethylamine, stearamidoethyldiethylamine, and mixtures thereof.

Commercially available amidoamines useful herein include: stearamidopropyldimethylamine with tradenames LEXAMINE S-13 available from Inolex (Philadelphia Pa., USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton N.J., USA).

Acid (ii) may be any organic or mineral acid which is capable of protonating the amidoamine in the hair treatment composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate all the amidoamine present, i.e. at a level which is at least equimolar to the amount of amidoamine present in the composition.

In conditioners of the invention, the level of cationic surfactant will generally range from 0.01 to 10%, more preferably 0.05 to 7.5%, most preferably 0.1 to 5% by weight of the composition.

Conditioners of the invention will typically also incorporate a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.01 to 10%, preferably from 0.1 to 8%, more preferably from 0.2 to 7%, most preferably from 0.3 to 6% by weight of the composition. The weight ratio of cationic surfactant to fatty alcohol is suitably from 1:1 to 1:10, preferably from 1:1.5 to 1:8, optimally from 1:2 to 1:5. If the weight ratio of cationic surfactant to fatty alcohol is too high, this can lead to eye irritancy from the composition. If it is too low, it can make the hair feel squeaky for some consumers.

Further Conditioning Agents

Compositions of the invention may comprise further conditioning agents to optimise wet and dry conditioning benefits.

Particularly preferred further conditioning agents are silicone emulsions.

Suitable silicone emulsions include those formed from silicones such as polydiorganosiloxanes, in particular polydimethylsiloxanes which have the CTFA designation dimethicone, polydimethyl siloxanes having hydroxyl end groups which have the CTFA designation dimethiconol, and amino-functional polydimethyl siloxanes which have the CTFA designation amodimethicone.

The emulsion droplets may typically have a Sauter mean droplet diameter ($D_{3,2}$) in the composition of the invention ranging from 0.01 to 20 micrometer, more preferably from 0.2 to 10 micrometer.

A suitable method for measuring the Sauter mean droplet diameter ($D_{3,2}$) is by laser light scattering using an instrument such as a Malvern Mastersizer.

Suitable silicone emulsions for use in compositions of the invention are available from suppliers of silicones such as Dow Corning and GE Silicones. The use of such pre-formed silicone emulsions is preferred for ease of processing and control of silicone particle size. Such pre-formed silicone emulsions will typically additionally comprise a suitable emulsifier such as an anionic or nonionic emulsifier, or mixture thereof, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874. In such materials, the silicone emulsion droplets are preferably formed from polydiorganosiloxanes such as those described above. One preferred form of the surface active block copolymer is according to the following formula:

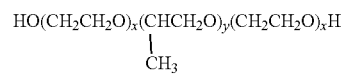

wherein the mean value of x is 4 or more and the mean value of y is 25 or more.

Another preferred form of the surface active block copolymer is according to the following formula:

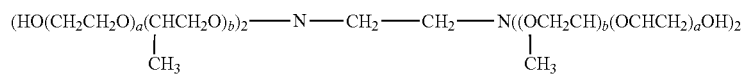

wherein the mean value of a is 2 or more and the mean value of b is 6 or more.

Mixtures of any of the above described silicone emulsions may also be used.

Silicone will generally be present in a composition of the invention at levels of from 0.05 to 10%, preferably 0.05 to 5%, more preferably from 0.5 to 2% by total weight of silicone based on the total weight of the composition.

Other Optional Ingredients

A composition of the invention may contain other ingredients for enhancing performance and/or consumer acceptability. Such ingredients include fragrance, dyes and pigments, pH adjusting agents, pearlescers or opacifiers, viscosity modifiers, preservatives, and natural hair nutrients such as botanicals, fruit extracts, sugar derivatives and amino acids.

Process

A particularly preferred process for preparing a hair care composition of the invention comprises a first step of blending the water-soluble, nonionic polymer of ethylene oxide with a carrier liquid, so as to form a slurry in which the polymer is coated with the carrier liquid. The slurry is then blended with the remaining composition ingredients using agitation to disperse the coating of carrier liquid.

Suitable carrier liquids may be any cosmetically acceptable material which does not dissolve the water-soluble, non-ionic polymer of ethylene oxide to any significant extent. Preferred examples include glycerine, oily hydrophobic perfumes and mixtures thereof.

Mode of Use

The compositions of the invention are primarily intended for topical application to the hair and/or scalp of a human subject in rinse-off compositions, in order to provide cleansing while improving hair fibre surface properties such as smoothness, softness, manageability, cuticle integrity, and shine. The compositions provided by the invention are preferably aqueous shampoo compositions, used by massaging them into the hair followed by rinsing with clean water prior to drying the hair. Optionally, a separate conditioning formulation may be applied after rinsing and before drying, but this may not be necessary as the aqueous shampoo compositions of the invention are intended to provide both cleansing and conditioning to the hair.

The invention is further illustrated with reference to the following, non-limiting examples, in which all percentages are by weight based on total weight unless otherwise specified.

EXAMPLES

Example 1 and Comparative Examples A, B and C

Shampoo compositions were prepared having ingredients as shown in the following Table. Example 1 represents a composition according to the invention and Examples A, B and C represent comparative examples.

| INGREDIENT | % weight | | | |
| --- | --- | --- | --- | --- |
| | Example 1 | Example A | Example B | Example C |
| Sodium lauryl sulphate | 6.0 | 6.0 | 6.0 | 6.0 |
| Cocamidopropyl betaine | 3.0 | 3.0 | 3.0 | 3.0 |
| Laureth-3-sulphosuccinate | 4.0 | 4.0 | 4.0 | 4.0 |
| Silicone[1] | 1.0 | 1.0 | 1.0 | 1.0 |
| Carbomer 980[2] | 0.6 | 0.6 | 0.6 | 0.6 |
| Guar hydroxypropyltrimonium chloride[3] | 0.2 | 0.2 | 0.2 | 0.2 |
| Preservative | 0.1 | 0.1 | 0.1 | 0.1 |
| Pearliser | 2.1 | 2.1 | 2.1 | 2.1 |
| Hydroxypropyl methylcellulose[4] | 0.2 | — | 0.2 | — |
| Polyethyleneoxide[5] | 0.1 | — | — | 0.1 |
| Water, minors | to 100 | to 100 | to 100 | to 100 |

[1]DC 1785 (an emulsion of dimethiconol with nonionic emulsifier from Dow Corning)
[2]CARBOPOL ® 980, from Goodrich.
[3]JAGUAR ® C13S, from Rhodia
[4]METHOCEL ® 40-202, from Amerchol Corporation (hydroxypropyl methylcellulose with viscosity of 4,000 mPa·s, for a 2% aqueous solution at 20° C., measured by Ubbelohde tube viscometer)
[5]POLYOX ® WSR-308, from Amerchol Corporation (a polyethyleneoxide having a $M_w$ of 8 million daltons and the CTFA designation PEG-180M)

The compositions of Examples 1, A, B and C were evaluated in a sensory test using 18 trained panellists. Various wet sensory attributes were ranked by the panellists on a 1 to 5 scale (1=low score; 5 maximum score) and the average scores are shown below.

| Composition | Attribute | | |
| --- | --- | --- | --- |
| | Wet Slippery Feel | Creamy Lather | Ease of Rinse |
| Ex.1 | 4.39 | 4.22 | 3.33 |
| Ex.A | 3.00 | 2.72 | 2.94 |
| Ex.B | 3.44 | 3.50 | 2.94 |
| Ex.C | 4.28 | 4.22 | 2.89 |

The results clearly show a superiority across all attributes tested, for the composition of Example 1, compared to either Example A, B or C.

The invention claimed is:

1. A hair care composition in the form of an aqueous shampoo composition comprising
    (i) from 5 to 20% by weight of anionic surfactants based on the total weight of the composition, wherein the anionic surfactants are sodium lauryl sulfate and Laureth-3-sulfosuccinate
    (ii) from 1 to 4% by weight of amphoteric surfactant based on the total weight of the composition, wherein the amphoteric surfactant is Cocoamidopropyl betaine
    (iii) from 0.02 to 0.2% by weight of nonionic polymer of ethylene oxide based on the total weight of the composition, wherein the non-ionic polymer of ethylene oxide is PEG-180M
    (iv) from 0.1 to 0.3% by weight of nonionic cellulose ether based on the total weight of the composition, wherein the nonionic cellulose ether is hydroxypropyl methyl cellulose with viscosity of 4,000 mPa·s
    (v) from 0.08 to 0.5% by weight of cationic polymer based on the total weight of the composition, wherein the cationic polymer is guar hydroxypropyl trimethylammonium chloride (vi) from 0.5 to 2% by weight of conditioning agent based on the total weight of the composition, wherein the conditioning agent is emulsion of dimethiconol wherein compositions comprising both nonionic polymer of ethylene oxide and nonionic cellulose ether have enhanced wet slippery feel and ease of rinse compared to use of identical composition where only one of the two nonionic polymers is used.

2. A method of cleansing hair comprising the application of a composition according to claim 1, followed by rinsing-off.

* * * * *